US009763890B2

(12) United States Patent
Lubitz et al.

(10) Patent No.: US 9,763,890 B2
(45) Date of Patent: Sep. 19, 2017

(54) BACTERIAL GHOSTS AS CARRIER AND TARGETING VEHICLES

(71) Applicant: Werner Lubitz, Kritzendorf (AT)

(72) Inventors: Werner Lubitz, Vienna (AT); Veronika Huter, Leobersdorf (AT)

(73) Assignee: WERNER LUBITZ, Klosterneuburg/Kritzendorf (AT)

( * ) Notice: Subject to any disclaimer, the term of this patent is extended or adjusted under 35 U.S.C. 154(b) by 0 days.

(21) Appl. No.: 15/091,825

(22) Filed: Apr. 6, 2016

(65) Prior Publication Data
US 2016/0220499 A1 Aug. 4, 2016

Related U.S. Application Data

(63) Continuation of application No. 13/282,144, filed on Oct. 26, 2011, now abandoned, which is a continuation of application No. 09/914,864, filed as application No. PCT/EP00/01906 on Mar. 3, 2000, now abandoned.

(30) Foreign Application Priority Data

Mar. 5, 1999 (DE) .................... 199 09 770

(51) Int. Cl.
A61K 9/50 (2006.01)
A61K 38/46 (2006.01)
A61K 48/00 (2006.01)
C12N 15/87 (2006.01)

(52) U.S. Cl.
CPC .......... A61K 9/5068 (2013.01); A61K 38/465 (2013.01); A61K 48/00 (2013.01); C12N 15/87 (2013.01); C12Y 301/03001 (2013.01)

(58) Field of Classification Search
None
See application file for complete search history.

(56) References Cited

U.S. PATENT DOCUMENTS

| 4,659,666 | A | 4/1987 | May et al. |
| 5,075,223 | A | 12/1991 | Lubitz et al. |
| 5,328,985 | A | 7/1994 | Sano et al. |
| 5,702,916 | A | 12/1997 | Molin et al. |
| 5,830,463 | A | 11/1998 | Duke et al. |
| 5,871,714 | A | 2/1999 | Budny |
| 2012/0040829 | A1 | 2/2012 | Lubitz et al. |

FOREIGN PATENT DOCUMENTS

| CA | 2263848 | 2/1998 |
| DE | 2541685 | 3/1977 |
| DE | 3919644 | 12/1990 |
| EP | 0242135 | 10/1987 |
| EP | 0291021 | 11/1988 |
| JP | 10510246 | 10/1998 |
| WO | 9113555 | 9/1991 |

OTHER PUBLICATIONS

Unpublished U.S. Appl. No. 09/914,864, filed Mar. 3, 2000.
U.S. Appl. No. 09/914,864, "Office Action", Feb. 10, 2011, 12 pages.
U.S. Appl. No. 09/914,864, "Office Action", Jul. 26, 2011, 12 pages.
U.S. Appl. No. 09/914,864, "US Patent Application", Dec. 3, 2001.
U.S. Appl. No. 13/282,144, "Advisory Action", Nov. 13, 2014, 3 pages.
U.S. Appl. No. 13/282,144, "Final Office Action", May 17, 2013, 11 pages.
U.S. Appl. No. 13/282,144, "Final Office Action", Jul. 31, 2014, 12 pages.
U.S. Appl. No. 13/282,144, "Final Office Action", Nov. 6, 2015, 13 pages.
U.S. Appl. No. 13/282,144, "Non-Final Office Action", Feb. 28, 2014.
U.S. Appl. No. 13/282,144, "Non-Final Office Action", Mar. 26, 2015, 13 pages.
U.S. Appl. No. 13/282,144, "Office Action", Jun. 27, 2012, 17 pages.
Argaraña et al., "Molecular Cloning and Nucleotide Sequence of the Streptavidin Gene", Nucleic Acids Res., vol. 14, No. 4, Feb. 1986, pp. 1871-1882.
Huter et al., "Bacterial Ghosts as Drug Carrier and Targeting Vehicles", Journal of Controlled Release, vol. 61, No. 1-2, Aug. 1999, pp. 51-63.
Laemmli, "Cleavage of structural Proteins during the Assembly of the Head of Bacteriophage T4", Nature, 1970, 227, pp. 680-685.
Lubitz et al., "Extended Recombinant Bacterial Ghost System", Journal of Biotechnology, vol. 73, No. 2-3, Aug. 1999, pp. 261-273.
Massie et al., "Molecular weight of the DNA in the chromosomes of *E. coli* and *B. subtilis*", Proc Natl Acad Sci U S A., 54, 1965, pp. 1636-1641.
Sone et al., "Roles of Disulfide Bonds in Bacterial Alkaline Phosphatase.", The Journal of Biological Chemistry, vol. 272, No. 10, 1997, 6174-78.
Steidler et al., "Functional Display of a Heterologous Protein on the Surface of *Lactococcus lactis* by Means of the Cell Wall Anchor of *Staphylococcus aureus* Protein A.", Applied Environmental Microbiology. vol. 61, No. 1, 1998, 342-45.
Szostak et al., "Bacterial Ghosts as Multifunctional Vaccine Particles", Behring Institute Mitteilugen, vol. 98, Feb. 1997, pp. 191-196.
Szostak, "Bacterial Ghosts: Non-living Candidate Vaccines", Journal of Biotechnology, vol. 44, Jan. 1996, pp. 161-170.
Towbin et al., "Electrophoretic Transfer of Proteins from Polyacrylarr.ide Gels to Nitrocellulose Sheets: Procedure and Some Applications", Biotechnology, vol. 24, Sep. 1992, pp. 145-149.
Waye et al., "EcoK Selection Vectors for Shotgun Cloning into M13 and Deletion Mutagenesis", Nucleic Acids Research, vol. 13(23), Dec. 1985, pp. 8561-8571.

(Continued)

Primary Examiner — Robert M Kelly
(74) Attorney, Agent, or Firm — Kilpatrick Townsend & Stockton LLP

(57) ABSTRACT

The invention concerns the use of bacterial ghosts as carrier and targeting vehicles for active substances.

11 Claims, 2 Drawing Sheets

(56) References Cited

OTHER PUBLICATIONS

Witte et al., "Endogenous Transmembrane Tunnel Formation Mediated by CPX174 Lysis Protein E, J. Bacteriol.", vol. 172, 1990, 4109-4114.

BACTERIAL GHOSTS AS CARRIER AND TARGETING VEHICLES

PRIOR RELATED APPLICATIONS

The present application is a continuation of U.S. patent application Ser. No. 13/282,144, filed Oct. 26, 2011, abandoned, which is a continuation of U.S. patent application Ser. No. 09/914,864, filed Sep. 4, 2001, abandoned, which is a U.S. National Phase application of International Patent Application No. PCT/EP00/01906, filed Mar. 3, 2000. The present application claims priority to German Patent Application No. 199 09 770.4, filed Mar. 5, 1999. Each of the foregoing applications is incorporated herein by reference in its entirety.

DESCRIPTION

The invention concerns the use of bacterial ghosts as carrier and targeting vehicles for encapsulated substances e.g. active substances.

Empty bacterial envelopes, so-called bacterial ghosts, can be produced in gram-negative bacteria by controlled heterologous expression of a gene which causes a partial lysis of the cell membrane (EP-A-0 291 021). An example of such a lytic gene is the gene E of the bacteriophage PhiX174 which codes for a polypeptide which is inserted into the cell wall complex of gram-negative bacteria and when oligomerized leads to the formation of a transmembrane tunnel structure through the inner and outer membrane. The inner diameter of this tunnel structure can be 40 to 200 nm or 500 to 1000 nm depending on the lysis conditions. The cytoplasmic material of the cell is released through this tunnel and leaves behind an empty cell envelope having an intact morphology. The use of bacterial ghosts as inactivated vaccines or adjuvants and the preparation of recombinant bacterial ghosts which carry heterologous surface proteins in their membrane is described in WO 91/13555 and WO 93/01791.

In addition ghosts can also be prepared from gram-positive bacteria by using a chimeric E-L lysis gene (U.S. Pat. No. 5,075,223).

It was surprisingly found that bacterial ghosts are exceptionally suitable as carriers or targeting vehicles for active substances. A first advantage of bacterial ghosts is that they can be administered without difficulty via the natural route of infection of pathogens such as via the respiratory or gastrointestinal tract. Moreover the system of administering active substances using ghosts as carriers provides an effective targeting due to the specificity of the bacterial ghosts for various types of tissue. As a result the active substance is transported very efficiently to the desired destination e.g. the corresponding potential site of infection of the initial bacteria. This advantage of using natural envelopes of pathogenic bacteria as vectors can only be achieved with difficulty and shortcomings using other forms of administration such as liposomes with incorporated external membrane proteins.

Since it is possible to prepare bacterial ghosts which only contain the desired active substance, a high degree of loading and thus a high efficiency of the active substance can be achieved. Moreover ghosts are a safe carrier material since they are not viable organisms. Finally the ghosts are products with a high immuno-stimulatory effect due to the presence of lipopoly-saccharides and peptidoglycans and hence it is not necessary to add additional adjuvants since the ghosts fulfil the adjuvant effect per se.

Hence one subject matter of the invention is the use of bacterial ghosts to package active substances.

A further subject matter of the invention is the use of bacterial ghosts as carrier or/and targeting vehicles for an active substance.

The active substance can be any desired active substance that can be transported into the interior of bacterial ghosts and can preferably be immobilized there. The active substance is preferably selected from pharmacologically active substances and labelling substances. Examples of pharmacologically active substances are polypeptides such as antibodies, therapeutically effective polypeptides such as cytokines, interferones, chemokines etc., enzymes and immunogenic polypeptides or peptides. Another example of active substances are nucleic acids in particular therapeutic nucleic acids e.g. nucleic acids for gene therapy which are preferably in the form of a vector that can be integrated into the chromosomes, or nucleic acids for a nucleic acid vaccination, antisense nucleic acids or ribozymes. Other examples of active substances are low-molecular active substances, peptides, hormones, antibiotics, anti-tumour agents, steroids, immunomodulators etc. The active substances can be present in the bacterial ghosts in a dissolved form, as suspensions or/and as emulsions optionally in combination with suitable carriers or/and auxiliary substances. In addition the active substances can also be diagnostical labelling-substances e.g. fluorescent substances, dyes or X-ray contrast media.

It is also possible to package non-medical active substances into the ghosts e.g. active substances from the field of agriculture such as insecticides, herbicides, agents against nematodes, enzymes for soil improvement, fertilizers, growth promoters, water-binding proteins to improve moisture penetration or water-binding in the atmosphere. Other applications are packaging of dyes for the printing industry e.g. forgery-proof inks that can be detected immunologically and the packaging of vitamins or probiotics for the food industry. It is also possible to package cosmetic agents or substances such as salts or other ionic substances.

The active substance is preferably present in the bacterial ghosts in an immobilized form i.e. the packaged active substance remains within the bacterial ghosts under physiological conditions for an adequate period to enable transport to the target cell or to the target tissue. The active substance can be immobilized by covalent or non-covalent interactions e.g. electrostatic interactions, high-affinity biological interactions, by mechanical retention or a combination of two or several of the said methods.

In a preferred embodiment of the invention the active substance is immobilized by means of direct or indirect interactions with a receptor which is located on the inside of the membrane e.g. the inside of the cytoplasmic membrane of the ghost as an integral membrane component or as a non-integral membrane component anchored to the membrane. The receptor can for example be a heterologous polypeptide which is integrated into the cytoplasmic membrane of the ghost by means of one or several membrane anchors and is produced in the bacterial cells before they are lysed to form ghosts by heterologous expression of appropriate fusion proteins which contain at least one membrane anchor domain and at least one receptor domain. Preferred examples of receptor domains are avidin or streptavidin which are able to form high-affinity bonds with biotin or biotin analogues. Streptavidin is particularly preferred. The anchoring of streptavidin in bacterial ghosts is preferably achieved by recombinant expression of a streptavidin fusion protein having a C-terminal membrane anchor in the cytoplasmic membrane of bacteria before the lysis leading to the formation of ghosts. In addition other receptor domains are also suitable e.g. antibody binding sites, lectins etc. which can bind with high affinity to a binding partner.

Alternatively it is also possible to not anchor the receptor to the membrane inner side until after lysis of the ghosts for example by using a receptor with two binding sites, one binding site being able to bind with high affinity to natural or recombinant structures on the inner side of the membrane and the second binding site being available for the direct or indirect immobilization of active substances.

A receptor molecule located on the inner side of the ghost membrane can directly or indirectly immobilize active substances inside the ghosts. In the case of a direct immobilization a receptor is selected which can interact sufficiently strongly with the active substance to be packaged in the ghosts in order to substantially or completely retain the active substance in the interior of the ghost. For this purpose one could for example use active substances modified with biotin, haptens or/and sugars which can bind in a stable manner to receptors such as streptavidin, antibodies or lectins. One preferably uses a modified active substance which carries one or several biotin groups and can bind with high affinity to a streptavidin receptor.

Alternatively it is also possible to indirectly immobilize the active substance on the receptor which is for example mediated by substances that bind the active substance and additionally have at least one additional binding site for the receptor. Examples of such active substance-binding substances are polymers e.g. proteins such as polylysin or polysaccharides such as protamine sulfate or dextran. The active substance-binding substances additionally carry receptor binding groups e.g. biotin or biotin analogues, haptens or sugar groups that can bind to lectins which are able to anchor them to the receptor located on the membrane.

The production of the ghosts loaded with active substances according to the invention comprises according to the aforementioned aspect of the invention firstly the preparation of bacterial ghosts by known methods e.g. by transforming the bacterial cell with a lysis gene, preferably the gene E of the phage PhiX174 or the chimeric E-L gene. The lysis gene is preferably expressed in the bacterial cell by a regulatable expression control sequence e.g. by the temperature-regulated promoter/repressor system $\lambda$-pR/c1857. With this expression control system the transformed bacteria are cultured at temperatures below 30° C. Increasing the temperature preferably to ≥40° C. inactivates the thermosensitive $\lambda$c1857 repressor and the lysis gene is expressed which leads to the formation of a transmembrane tunnel structure in the cell envelope resulting in lysis of the cells within a few minutes. The use of mutated $\lambda$ promoter/operator systems allows the bacteria to also be cultured at higher or lower temperatures e.g. 37° C. (WO 98/07874). The bacterial ghosts can then be harvested by centrifugation and used for loading with active substances after washing and optionally freeze-drying. For this purpose the ghosts are contacted with a solution or/and suspension containing the active substance to be packaged under conditions which allow adequate amounts of active substance to penetrate into the bacterial ghosts. If necessary receptor substances are also added which enable the molecules of the active substance to be immobilized on the inside of the ghost membrane. The receptor molecules can be added before, at the same time as or after contacting the ghosts with the active substance to be packaged.

Alternatively or/and in addition the active substance can be immobilized by forming a matrix in the interior of the ghost. This matrix is preferably a polymer matrix which is formed in situ in the interior of the ghost and prevents active substances from diffusing out of the ghosts. The polymer matrix can be produced by polymerization or/and copolymerization of suitable monomers or/and by storing together aggregatable substances in the interior of the bacterial ghosts. The polymerization can be started by setting up appropriate conditions e.g. by increasing the temperature, UV radiation or/and adding suitable initiators. It is expedient to use physiologically tolerated monomers such as hydroxyfatty acids, amino acids, saccharides or derivatives thereof which result in the formation of a polymer that can be degraded in the body under physiological conditions.

The matrix is particularly preferably produced by enzyme-catalysed polymer formation. For this purpose suitable enzymes are immobilized on the inner wall of the bacterial ghosts for example by integration into the inner wall of the cytoplasmic membrane (as described for streptavidin) or indirectly e.g. by binding biotinylated enzymes to streptavidin molecules on the ghost inner membrane. Enzymes can for example be used for this purpose which catalyse the synthesis of polyhydroxyfatty acids e.g. polyhydroxybutyric acid such as PHB-synthase, polysaccharides such as glucosyl transferases or polypeptides such as non-ribosomal polypeptide-synthesizing enzymes which occur in peptido-glycan synthesis. The polymer formation resulting from the addition of suitable monomers and optionally biochemical energy equivalents such as ATP in the presence of the enzymes results in that the active substances located in the ghost interior are cocooned in the matrix formed by the enzymes and thus retain inside the ghost.

Alternatively the matrix can also be formed by the aggregation of substances capable of aggregation e.g. molecules or colloidal particles. This aggregation can be initiated by changing the ambient conditions e.g. changing the temperature or/and pH.

In those embodiments of the invention in which the active substances are immobilized by being bound to a matrix in the inside of the ghosts, the active substances to be encapsulated are firstly introduced into the ghosts and subsequently the matrix is formed.

The ghosts according to the invention with the active substances encapsulated therein are extremely suitable as carrier and targeting vehicles since the ghosts because of their properties as bacterial envelopes already preferably attach themselves to certain cell types or are taken up by cells of the immune system. This targeting can be further improved by using ghosts with modified envelopes i.e. ghosts which carry target-specific surface molecules on the outer side of their membranes i.e. surface molecules which are specific for target cells or a target tissue. The introduction of these target-specific molecules such as sugars e.g. mannose or fucose, or invasin from *Yersinia* or invasin derivatives can be achieved by recombinant expression of appropriate fusion polypeptides in the bacterial cell before lysis or/and by attachment using a suitable receptor system (e.g. streptavidin/biotin).

One embodiment of the invention is to use the ghosts containing the active substances for medical purposes. The administration of active substances e.g. pharmacologically active substances, antigens, antibodies or nucleic acids by means of ghosts is suitable for preventing or/and combating all types of diseases e.g. for combating diseases caused by pathogens such as viruses, bacteria, parasites or fungi or for preventing or/and combating tumour or autoimmune diseases or for gene therapy. In this case a substance effective against the respective disease is used as the active substance which becomes physiologically active after transport to and optionally internalisation in the target cell. The present invention also enables the administration of combinations of active substances i.e. the ghosts can contain several different active substances or mixtures of ghosts each containing different active substances can be used. In addition the administration of active substances by means of ghosts can also be used for diagnostic purposes (imaging).

A particularly preferred application is the use of bacterial ghosts as carrier and targeting vehicles for gene therapy. The poor specificity of existing nucleic acid vehicles such as liposomes can be decisively improved by packaging nucleic acids such as DNA or RNA into ghosts. The advantage of bacterial ghosts as carrier vehicles is that they have a high capacity for loading with nucleic acids. In addition they are safe as vectors since they are not living cell envelopes. In applications in gene therapy the nucleic acids in the ghosts can for example be complexed with polyhydroxy-alkanoates e.g. polyhydroxybutyric acid or copolymers of hydroxybutyric acid with other hydroxyfatty acids such as 3-hydroxytridecanoic acid. In this connection the nucleic acids can be immobilized in a growing polymer matrix or complexes can be prepared from nucleic acids and amorphous polyhydroxyfatty acid granula. Another method of encapsulating nucleic acid in bacterial ghosts is to use DNA binding proteins such as polylysine or protamines which are globular, strongly alkaline proteins of a relatively low molecular weight between 1000 and 5000. Protamines can be isolated in the form of crystalline salts e.g. protamine sulfate from defatted bird or fish sperm by shaking with dilute acids. Protamines can be incorporated into the membrane of ghosts in the form of fusion proteins or alternatively they can be anchored to membrane-bound streptavidin in the ghosts by biotinylation.

Another particularly preferred application is the use of bacterial ghosts to prepare a nucleic acid vaccine in particular a DNA vaccine and the use of bacterial ghosts as carrier or/and targeting vehicles for a nucleic acid vaccine in particular for a DNA vaccine.

Bacterial ghosts as carrier or targeting vehicles for nucleic acid vaccination result in the development of an effective and long-lasting specific immune response. The bacterial ghosts containing the nucleic acids are taken up by primary antigen-presenting cells (APC) such as dendritic cells and macrophages by means of specific receptors and fragmented into antigenic peptides. In addition the antigen which is coded by the packaged DNA sequence is expressed with high efficiency in the APC. As a result the antigen is presented on the surface of the APC in association with MHC-I or/and MHC-II structures of the T lymphocytes and can induce an immune response. In this connection investigations have shown that antigen processing and presentation by MHC-I and II complexes take place which induces a humoral and cellular immune response like that which is also observed in the case of bacterial infections with live germs.

The nucleic acid packaged in the bacterial ghosts is preferably in a form that cannot be replicated in the recipient organism. It contains a sequence which codes for the antigen to be expressed in the target cell in a form that is capable of expression i.e. in operative linkage with active expression control sequences in the target cell such as promoters and optionally enhancers to allow a high gene expression, polyadenylation sequences to ensure a correct termination of the transcribed mRNA or/and translation initiation sequences to enable a high protein production. In addition the nucleic acids can contain a bacterial origin of replication which allows the amplification of large amounts of nucleic acid in bacteria such as *E. coli*, a prokaryotic selection marker gene e.g. for antibiotic resistance, a reporter gene which allows a simple determination of the expression rate e.g. the GFP gene or/and immunomodulatory sequences.

The nucleic acid is preferably a DNA, particularly preferably a plasmid DNA which can be present in a circular or/and linear form. However, the use of RNA vaccines or vaccines based on nucleic acid analogues that can be transcribed but have an increased physiological stability is also conceivable.

The promoter driving the expression of the antigen-coding sequence is preferably a strong viral promoter/enhancer e.g. the rous sarcoma virus (RSV) promoter/enhancer, the murine leukaemia virus (MLV) promoter/enhancer, the SV40 promoter/enhancer and particularly preferably the cytomegalovirus (CMV) promoter/enhancer. The polyadenylation sequences from SV40 or from the bovine growth hormone gene but preferably from the rabbit β-globin gene can be used as transcription terminators.

The antigen that is used in this connection is a polypeptide or a peptide fragment thereof that is associated with the respective disease and which induces an immune response after expression in the target cell. The present invention also enables combination vaccines to be administered i.e. the ghosts can contain several different antigen-coding nucleic acids which can for example be derived from the same pathogen or from different pathogens or it is possible to use mixtures of ghosts each containing different antigen-coding nucleic acids.

In one embodiment of the invention so-called homologous combinations of bacterial ghost and antigen-encoding nucleic acid can be used in which case the bacterial ghost for example carries surface structures which are derived from the same species or from the same organism as the antigen coded by the nucleic acid vaccine. The ghost may even carry a surface structure corresponding to the encoded antigen on its surface. This homologous ghost/nucleic acid combination is especially suitable for vaccinating against bacterial infections but can be also extended to vaccinating against other diseases such as viral diseases by using recombinant ghosts with appropriate surface structures.

Alternatively a heterologous ghost/nucleic acid combination is used. In such a heterologous combination the bacterial ghost in general has an adjuvant function. However, embodiments are also possible in which a ghost derived from a pathogenic bacterium is used in combination with a heterologous nucleic acid as a combination vaccine against two different pathogens.

Finally bacterial ghosts are also suitable as carrier or targeting vehicles for the agricultural field in which they can be used to apply active substances such as herbicides, fungicides or/and insecticides.

The ghosts are particularly preferably derived from gram-negative bacteria which are for example selected from *Escherichia coli, Klebsiella, Salmonella, Enterobacter, Pseudomonas, Vibrio, Actinobacillus, Haemophillus, Pasteurella, Bordetella, Helicobacter, Francisella, Brambamella, Erwinia, Pantoea, Streptomyces, Frankia, Serratia, Agrobacterium, Azotobacter, Bradyrhizobium, Burkholderia, Rhizobium, Rhizomonas* and *Sphingomonas. Staphylococcus, Streptococcus* and *Bacillus* are particularly preferred examples of gram-positive bacteria.

The ghosts containing active substances can be administered pharmaceutically by common methods; for example by oral, aerogenic e.g. intranasal, intraocular, topical or parenteral, e.g. intramuscular, intraperitoneal, intravenous or subcutaneous administration.

The ghosts are preferably administered by the same route as the natural infection of the organism with the pathogen. Hence bacterial ghosts containing substances that are active against pathogens whose main portal of entry is the gastrointestinal tract (*E. coli, Salmonella, Vibrio* or *Helicobacter*) can be administered orally. Ghosts from pneumonia pathogens containing appropriate active substances e.g. *Actinobacillus, Pasteurella, Pseudomonas* or *Haemophilus* are preferably administered aerogenically.

The administration of bacterial ghosts containing active substances according to the invention is not only suitable for human medicine but also for veterinary medicine and in particular for the protective vaccination of domestic animals such as pigs, cows etc.

For agricultural forms of application the ghosts can be applied via the soil, the air or as capsules on seeds.

The application of active substances by means of bacterial ghosts has numerous advantages over previous forms of application. Thus small amounts of active substance are already sufficient to achieve a strong effect. Moreover target cell/tissue-specific administration of the active substances is possible. An adjuvant effect is achieved because the bacterial ghost envelopes already have an immunogenic effect. The active substance enclosed in the ghost is protected against degradation by physiological processes, e.g. by enzymes such as proteases, nucleases or hydrolases. Moreover a combination with other active substances is possible. Finally the bacterial ghosts can be produced cost-effectively and the active substances can be simply and cost-effectively formulated.

Yet another subject matter of the invention are bacterial ghosts containing an active substance encapsulated therein and the active substance can for example be a nucleic acid.

Finally the invention also concerns a pharmaceutical or agricultural composition comprising a bacterial ghost containing an active substance packaged therein. The pharmaceutical composition according to the invention can be present in the form of conventional pharmaceutical preparations e.g. as an injectable or aerogenically administrable solution or suspension, as an oral preparation e.g. as a tablet, capsule or dragee, as a cream or ointment etc. Furthermore the composition can be present as a lyophilisate to be reconstituted.

The composition according to the invention is obtainable by a process comprising the steps:
providing bacterial ghosts and
contacting the bacterial ghosts with an active substance under conditions which lead to a packaging and preferably to an immobilization of the active substance in the ghosts.

The invention is further elucidated by the following figures and examples.

EXAMPLES

1. Materials and Methods
1.1 Construction of Streptavidin-Encoding Plasmids

Figure 1:
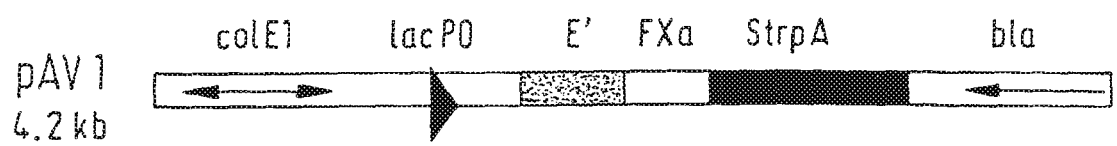
FIG. 1 shows a schematic representation of the streptavidin-anchoring plasmid pAV1 which contains a fusion gene E'-FXa-StrpA under the control of the inducible lac promoter (lacPO), the origin of replication ColE1 and the ampicillin resistance gene bla.

The plasmid pBGG9 (British Biotechnology Limited) was cleaved with the restriction enzymes NdeI and HindIII. A 495 by DNA fragment containing the complete streptavidin gene (Argarana et al., Nucleic acids Res. 14 (1986), 1871-1882) was isolated by agarose gel electrophoresis and subsequent electroelution. The NdeI restriction site was filled in by Klenow polymerase and the fragment was inserted between the HincII and HindIII restriction sites of M13K11RX (Waye et al., Nucleic acids Res. 13 (1985), 8561-8571) The resulting phagemid M13FN contains 160 codons of the streptavidin gene fused to the 3'-end of a short sequence which codes for the recognition sequence ile-glu-gly-arg of the protease factor Xa (FXa). This FXa-StrpA cassette was isolated by restriction cleavage with BamHI and the resulting 509 by DNA fragment was subcloned into the BamHI-linearized plasmid pSK (Stratagene, Cleveland, Ohio) to create the plasmid pFN6. The same 509 by BamHI fragment was also inserted into the BamHI-cleaved membrane targeting vector pKSEL5 to obtain the plasmid pAV1 containing the streptavidin gene fused to the 5'-terminal membrane anchor sequence E' (FIG. 1).

1.2 Preparation of Streptavidin Ghosts

*E. coli* NM522 cells (Stratagene) were simultaneously transformed with the lysis plasmid pML1 (Szostak et al., J. Biotechnol. 44 (1996), 161-170) and the streptavidin-encoding plasmid pAV1. The transformants were cultured at 28° C. in LB medium (10 g/l tryptone, 5 g/l yeast extract, 5 g/l NaCl) containing ampicillin (200 µg/ml) and kanamycin (50 µg/ml). One liter of medium was inoculated with an overnight culture which was derived from a single transformant colony and used as a preculture for a fermenter (type MRD 60TE, Meredos GmbH, Bovenden, Germany). The bacteria were cultured in the fermenter in a volume of 10 l with aeration and agitation until an optical density at 600 nm of 0.4 was reached. IPTG was then added to a final concentration of 3 mM in order to induce the expression of streptavidin. After 30 min 0.2 M $MgSO_4$ was added and 20 min thereafter the expression of the lysis protein E was induced by increasing the temperature from 28° C. to 42° C. After 1 h the cells were harvested by centrifugation at 4000 g. Resuspension of the pellets in distilled water (final volume 5 l) led to their immediate lysis. The ghosts were washed twice in a large volume of Tris-buffered saline (TBS) and subsequently lyophilized.

1.3 Light and Electron Microscopy

Examinations by light microscopy were carried out using an Olympus AX70 True Research System Microscope. Transmission electron micrographs were taken with a Siemens Elmiscop 101 electron microscope. Scanning electron micrographs were taken with a Hitachi S-800 field emission scanning electron microscope. The fixation of cells and preparation for electron microscopy were carried out as described by Witte et al. (J. Bacteriol. 172 (1990), 4109-4114).

For the detection of streptavidin the ghosts were incubated while shaking for 20 min at 37° C. with gold-labelled albumin-biotin (10 nm, Sigma Immunochemicals) diluted in Tris buffer (10 mM Tris, 150 mM NaCl, pH 7.4), washed, and fixed for electron microscopy.

1.4 SDS-polyacrylamide Gel Electrophoresis and Western Blot

Ghosts or protein samples were boiled for 5 min in gel loading buffer (2% SDS, 5% 2-mercaptoethanol, 10% glycerol and 0.003% bromophenol blue in 0.063 M Tris-HCl buffer, pH 6.8) and separated on a 10% SDS-polyacrylamide gel by the method of Laemmli (Nature 227 (1970), 680 to 685). Western blots were carried out as described by Towbin et al (Biotechnology 24 (1992), 145-149). Blots were blocked in TBS containing 1% bovine serum and incubated with anti-streptavidin antiserum from rabbits (Sigma Immunochemicals).

1.5 Binding of Biotinylated Alkaline Phosphatase and Fluorescent-Labelled Biotin Biotinylated alkaline phosphatase (Pierce) was diluted 1:1000 in Tris buffer. 2 mg of lyophilized ghosts was suspended in 500 μl diluted alkaline phosphatase solution and incubated for 30 min at 37° C. while shaking. The samples were centrifuged at 10000 g and washed three times in 20 ml Tris buffer and a fourth time in diethanolamine buffer (10 mM diethanolamine, 0.5 mM $MgCl^2$, pH 9.5) and subsequently divided into six aliquots. Substrate (2.5 mM p-nitrophenyl phosphate in diethanolamine buffer) was added and the reactions were stopped after 0.5, 1, 2, 4, 8 or 16 min by adding an equal volume of 7 M NaOH. The samples were centrifuged at 10000 g and the supernatants were measured at 410 nm.

A molar absorption coefficient $\epsilon=18.5\times10^{3x}M^{-1}\times cm^{-1}$ was determined and used to calculate the amount of p-nitrophenol formed according to the Lambert-Beer equation. The number of molecules of alkaline phosphatase bound per ghost was calculated assuming that one unit of alkaline phosphatase activity corresponds to the release of 1 μmol nitrophenol per min at pH 9.5 and 37° C. One unit of alkaline phosphatase corresponds to 0.7 μg, its molecular weight is 140000 and 1 mg of ghosts contains $6.7\times10^8$ individual envelopes.

For the binding of fluorescent-labelled biotin (FITC-biotin), ghosts were washed repeatedly in PBS until the relative fluorescence intensity in the supernatants was less than 0.5 at 530 nm (excitation at 490 nm). 1 mg lyophilized ghosts was incubated while shaking for 30 min in 2 ml of a solution containing 0.4056 μg FITC-biotin/100 ml TBS. The samples were centrifuged at 10000 g and the fluorescence intensities were measured in the supernatants.

1.6 Biotinylation of Polylysine

Poly-L-lysine hydrobromide, molecular weight 18000 (Sigma), was biotinylated using the following protocol: 6 mg polylysine was taken up in 1 ml phosphate-buffered saline (PBS). 50 μl of a solution of 640 μg biotin-N-hydroxysuccinimide ester (Boehringer Mannheim) in 200 μl DMSO was added and the pH was adjusted to 10 using 0.5 M NaOH. The reaction mixture was stirred overnight at room temperature and subsequently dialysed for 48 h against water. A HABA test (Sigma) yielded a binding ratio of 2 mol biotin per mol polylysine.

1.7 Fluorescent Labelling of DNA

A randomly selected plasmid (pUC18) was used to generate fluorescent-labelled DNA. Labelling was carried out using the polymerase chain reaction and labelled nucleotides (Cy3-dCTP, Pierce). The reaction mixtures contained 200 μM dATP, 200 μM dGTP, 200 μM dTTP, 200 μM dCTP (75% thereof is Cy3-dCTP), 1 μM of each oligonucleotide primer, 0.2 ng/μl linearized plasmid DNA and 0.02 U/μl Taq DNA polymerase in polymerase buffer. The reaction protocol was as follows: predenaturation for 4 min at 95° C.; 35 cycles: 1 min 95° C./1 min 60° C./3 min 72° C.; 5 min final extension at 72° C. The samples were phenolized, precipitated with ethanol, resuspended in 10 mM Tris-HCl (pH 8.0) and stored at −20° C.

1.8 Binding of Fluorescent-Labelled Dextran and DNA/Polylysine.

1 mg lyophilized streptavidin-ghosts was suspended in 1 ml Tris buffer. 50 μl of an aqueous solution (1 mg/ml) of biotinylated fluorescent-labelled dextran (Molecular Probes Europe BV) was added and the mixture was incubated for 1 h at 37° C. while shaking. The ghosts were washed three times in 1.5 ml Tris buffer and analysed by light microscopy. Diluted solutions of DNA (0.1 μg/μl in HBS [150 mM NaCl, 20 mM HERPES, pH 7.3]) and poly-L-lysine (1 μg/μl in HBS) were prepared in order to form complexes of fluorescent-labelled DNA and biotinylated polylysine. The solutions were combined at a weight ratio of DNA to polylysine of 10:1 and mixed rapidly. Streptavidin-ghosts were suspended therein, incubated for 1 h at 37° C. while shaking, washed and analysed by light microscopy.

2. Results 2.1 Membrane Anchoring of Streptavidin

If the bacterial ghosts are used as a vehicle to transport active substances, the active substance should be fixed within the bacterial envelope. Recombinant ghosts which contain streptavidin anchored in their envelope are able to bind biotinylated compounds with high affinity. The plasmid pAV1 was constructed for this as described in section 1.1. It contains a hybrid gene consisting of the 54 5'-terminal codons of gene E of the bacteriophage PhiX174 (E') followed by an in frame-fusion of the FXa-StrpA cassette. This plasmid is shown schematically in FIG. 1.

2.2 Production of Streptavidin-Ghosts

Several E-specific lysis plasmids with different gene E expression control sequences, origins of replication and selection marker genes are available (Szostak et al., J. Biotechnol. 44 (1996), 161-170). The plasmid pML1 used here contains the gene E under the transcriptional control of the $\lambda P_R$-c1857 system. Onset of lysis can be observed in the E. coli strain NM522/pML1 by a decrease of optical density at 600 nm approximately 10 min after increasing the culturing temperature from 28° C. to 42° C.

For the production of ghosts by an alternative E-lysis protocol, 0.2 M $MgSO_4$ was added to the culture medium 20 min prior to inducing gene E expression. In this procedure protein E is incorporated into the bacterial cell wall complex, but cell lysis is inhibited by the high salt concentration in the surrounding medium. Gene E expression is allowed to proceed for 1 h in cultures treated with $MgSO_4$ and the cells are subsequently harvested by centrifugation. Resuspension of these cells in water or low ionic strength buffers results in immediate, explosive lysis which creates substantially larger lysis holes than normal E-lysis.

2.3 Microscopic Visualisation of Ghosts Produced by Alternative Lysis

Ghosts can be distinguished from living cells by light microscopic examination in which they appear distinctly more transparent than intact bacteria. Examination of ghosts by light microscopy which have been produced by alternative E-lysis showed cells exhibiting polar caps that had been blasted off or cracks in the middle opening them up into two halves. The ghosts appeared slightly elongated.

2.4 Detection of Streptavidin with Gold-Conjugated Biotin

In order to detect the localization of streptavidin in the ghosts, streptavidin-ghosts were incubated with gold-labelled albumin-biotin particles, washed and examined by electron microscopy. Ultrathin sections revealed gold particles distributed exclusively along the inner membrane of the ghosts.

2.5 Determination of Streptavidin Anchorage in Ghosts

Streptavidin-ghosts were analysed by SDS-polyacrylamide gel electrophoresis together with defined amounts of pure streptavidin as a control in order to determine their streptavidin content. The gels were transferred onto nitrocellulose membranes and treated with anti-streptavidin antiserum. Densitometric analysis of the streptavidin-specific bands on Western blots revealed a streptavidin content of approximately 5% of the total cell weight.

2.6 Functional Binding of Biotinylated Alkaline Phosphatase and FITC-Biotin, and Quantification of the Binding Sites An enzymatic assay was developed to determine the biotin-binding capacity of streptavidin-ghosts. Streptavidin-ghosts and streptavidin-negative ghosts (ghosts without streptavidin anchored to their membrane) which had both been prepared by the alternative lysis protocol, and streptavidin-ghosts produced by standard lysis, were incubated with biotinylated alkaline phosphatase. After extensive washing, the amount of retained enzyme was measured using p-nitrophenyl nitrophosphate as a substrate. Whereas almost no reaction was observed in streptavidin-negative ghost samples, alternatively lysed streptavidin-ghosts exhibited a bright yellow colouration. The reaction was stopped after controlled intervals and the absorbance of the sample supernatants was measured at 410 nm.

The number of molecules of alkaline phosphatase bound per ghost was determined as approximately 200 by the calculation method described in section 1.5. Interestingly, streptavidin-ghosts produced by normal lysis were negative in the enzymatic test. Consequently, the larger holes created by the alternative lysis protocol are necessary for large molecules of active substances like alkaline phosphatase to allow an efficient diffusion into the interior of the ghosts.

Figure 2:
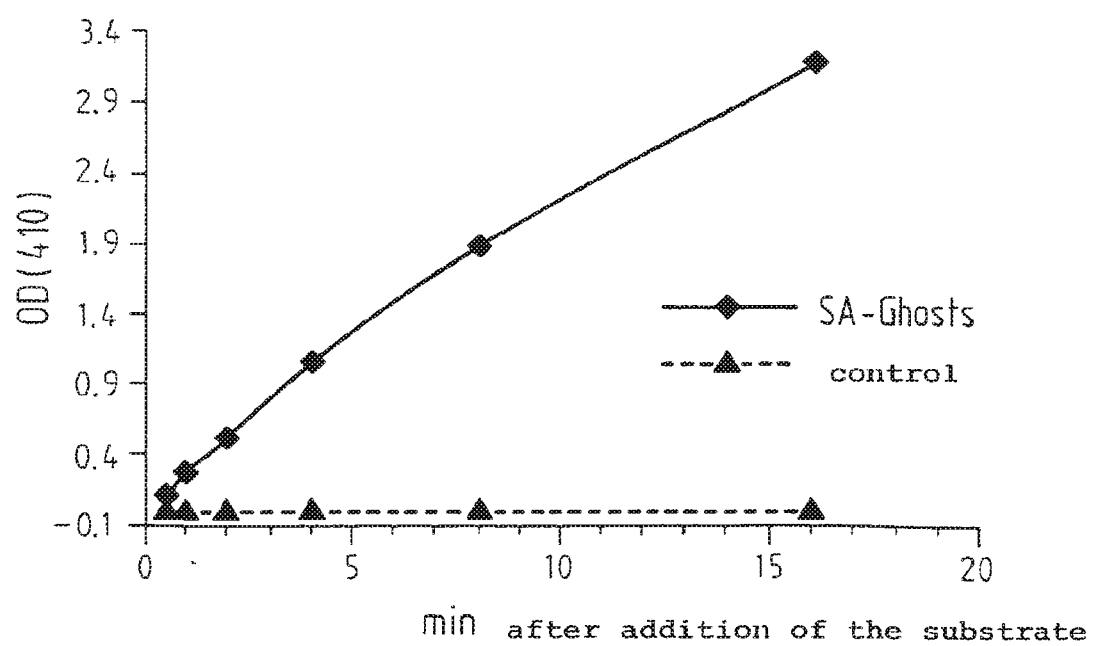
FIG. 2 shows the reaction kinetics of alkaline phosphatase bound in streptavidin ghosts.

FIG. 2 shows the kinetics of the reaction of biotinylated alkaline phosphatase which was bound to streptavidin-ghosts produced by alternative lysis. Streptavidin-negative ghosts produced by alternative lysis were used as a control.

A similar test was carried out using fluorescent-labelled biotin. Ghost and streptavidin-ghost samples were incubated with FITC-biotin, centrifuged and the residual fluorescence of unbound label was measured in the supernatants. The number of these much smaller molecules (molecular weight 832) that were bound was 2060.+−0.400 per ghost.

2.7 Binding of Fluorescent-Labelled Biotinylated Dextran and Fluorescent-Labelled DNA Fluorescent-labelled biotinylated dextran and fluorescent-labelled DNA were used as a model to demonstrate the fixation of compounds that could be used for the targeting of active substances in streptavidin-ghosts. For this streptavidin-ghosts were incubated with a mixture of biotinylated poly-L-lysine and fluorescent-labelled DNA or with fluorescent-labelled biotinylated dextran and analysed by fluorescence light microscopy. In both cases the fluorescent label was detected on the ghosts. Negative controls (ghosts without streptavidin) were not stained.

The invention claimed is:

1. A method for preparation of a bacterial ghost containing an active substance encapsulated therein, comprising:
  (i) preparing a bacterial ghost comprising a receptor, wherein the receptor is a heterologously expressed polypeptide integrated into a cytoplasmic membrane of the bacterial ghost comprising the receptor, and
  (ii) encapsulating the active substance in the bacterial ghost comprising the receptor prepared in step (i), wherein the active substance is present in the bacterial ghost in the immobilized form by interactions with the receptor.

2. The method of claim 1, wherein the active substance is immobilized on the receptor by non-covalent interactions.

3. The method of claim 1, wherein the active substance is immobilized on the receptor by non-covalent interactions that are not antibody-antigen binding.

4. The method of claim 1, wherein the active substance is not an antibody.

5. The method of claim 1, wherein the active substance is immobilized by non-covalent interactions between avidin or streptavidin and biotin or biotin analogs on the receptor located on an inner side of the cytoplasmic membrane of the bacterial ghost.

6. The method of claim 1, wherein the heterologously expressed polypeptide is a fusion polypeptide.

7. The method of claim 1, wherein the heterologously expressed polypeptide is a fusion polypeptide containing streptavidin or avidin.

8. The method of claim 1, wherein the active substance is a fusion polypeptide.

9. The method of claim 1, wherein the active substance is derivatized with receptor binding groups.

10. The method of claim 1, wherein the active substance is a biotinylated active substance.

11. The method of claim 1, wherein the active substance is biotinylated alkaline phosphatase.

* * * * *